(12) United States Patent
Kamikonya et al.

(10) Patent No.: US 7,460,640 B2
(45) Date of Patent: Dec. 2, 2008

(54) RADIOTHERAPY MONITORING APPARATUS

(75) Inventors: Norihiko Kamikonya, 13-22, Hinomine 1-chome, Kita-ku, Kobe, Hyogo-ken (JP); Takayuki Kuwahara, Otawara (JP)

(73) Assignees: Norihiko Kamikonya, Kobe-shi (JP); Toshiba Medical Systems Corporation, Otawara-shi (JP)

( * ) Notice: Subject to any disclaimer, the term of this patent is extended or adjusted under 35 U.S.C. 154(b) by 22 days.

(21) Appl. No.: 11/549,307

(22) Filed: Oct. 13, 2006

(65) Prior Publication Data

US 2007/0140425 A1    Jun. 21, 2007

(30) Foreign Application Priority Data

Oct. 14, 2005    (JP) .............................. 2005-299620

(51) Int. Cl.
*A61N 5/10* (2006.01)

(52) U.S. Cl. ....................................................... 378/65

(58) Field of Classification Search .................. 378/51, 378/64, 65, 97, 114, 115, 117; 382/128, 382/132; 600/1, 2, 407, 436
See application file for complete search history.

(56) References Cited

U.S. PATENT DOCUMENTS

| | | | | |
|---|---|---|---|---|
| 6,113,264 | A  * | 9/2000 | Watanabe | ................... 378/197 |
| 2004/0034269 | A1* | 2/2004 | Ozaki | ............................ 600/1 |
| 2004/0131145 | A1* | 7/2004 | Ohara | ......................... 378/37 |

* cited by examiner

*Primary Examiner*—Edward J Glick
*Assistant Examiner*—Mona M Sanei
(74) *Attorney, Agent, or Firm*—Oblon, Spivak, McClelland, Maier & Neustadt, P.C.

(57) ABSTRACT

A radiotherapy monitoring apparatus for monitoring a treatment state by irradiation of radiations on a treatment region includes a flat panel detector that detects the radiations transmitted through the treatment region at least in two places, a comparing unit that compares a relative value of the transmitted radiations in the two places with a reference relative value, and control signal generating units that generate, when the relative value exceeds the reference relative value, a control signal for stopping the irradiation of the radiations.

20 Claims, 6 Drawing Sheets

RADIOTHERAPY MONITORING APPARATUS

CROSS-REFERENCE TO RELATED APPLICATIONS

This application is based upon and claims the benefit of priority from prior Japanese Patent Application No. 2005-299620, filed Oct. 14, 2005, the entire contents of which are incorporated herein by reference.

BACKGROUND OF THE INVENTION

1. Field of the Invention

The present invention relates to a radiotherapy monitoring apparatus that instantaneously monitors a state of radiotherapy for irradiating radiations on a focus region such as cancer to treat the focus region.

2. Description of the Related Art

Conventionally, the radiotherapy for irradiating radiations on a lesion region such as cancer has been performed in the clinical field. Effectiveness of the radiotherapy has been recognized. As a radiotherapy apparatus for performing the radiotherapy, a linear accelerator is used. The linear accelerator irradiates radiations on an affected area of a patient lying on a treatment bed. Various kinds of prior preparation work are necessary in order to treat the patient using such a radiotherapy apparatus. First, images of a disease region are acquired by a visualizing apparatus such as an X-ray computerized tomographic apparatus and plans a field of view, an angle, the number of fields, and the like using the images such that the radiations can be limitedly irradiated on the affected area as much as possible.

In recent years, under the circumstances in which various approaches for cancer treatment have been attempted, the significance of the radiotherapy as a radical therapy has been recognized again. According to an increase in opportunities of such radiotherapy, it is demanded to establish a highly accurate treatment monitoring system and realize qualitative improvement and high safety of the radiotherapy.

BRIEF SUMMARY OF THE INVENTION

It is an object of the invention to realize improvement of monitoring accuracy of the radiotherapy in a radiotherapy monitoring apparatus.

According to a first aspect of the invention, there is provided a radiotherapy monitoring apparatus for monitoring a treatment state by irradiation of radiations on a treatment region, including: a detecting unit that detects the radiations transmitted through the treatment region at least in two places; a comparing unit that compares a relative value of the transmitted radiations in the two places with a reference relative value; and a control signal generating unit that generates, when the relative value exceeds the reference relative value, a control signal for stopping the irradiation of the radiations.

According to a second aspect of the invention, there is provided a radiotherapy monitoring apparatus for monitoring a treatment state by irradiation of radiations on a treatment region, including: a reference value calculating unit that calculates at least one of a ratio of exit doses in at least two places in an irradiation range of the radiations and an absolute value of a difference between the exit doses as a reference value on the basis of a planned dose distribution; a detecting unit that detects the radiations transmitted through the treatment region; a measured value calculating unit that calculates at least one of the ratio of the exit doses in the two places and the absolute value of the difference between the exit doses as a measured value on the basis of an output of the detecting unit; a comparing unit that compares the measured value with the reference value; and a control signal output unit that outputs a control signal corresponding to a result obtained by comparing the measured value with the reference value.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Figure 1:
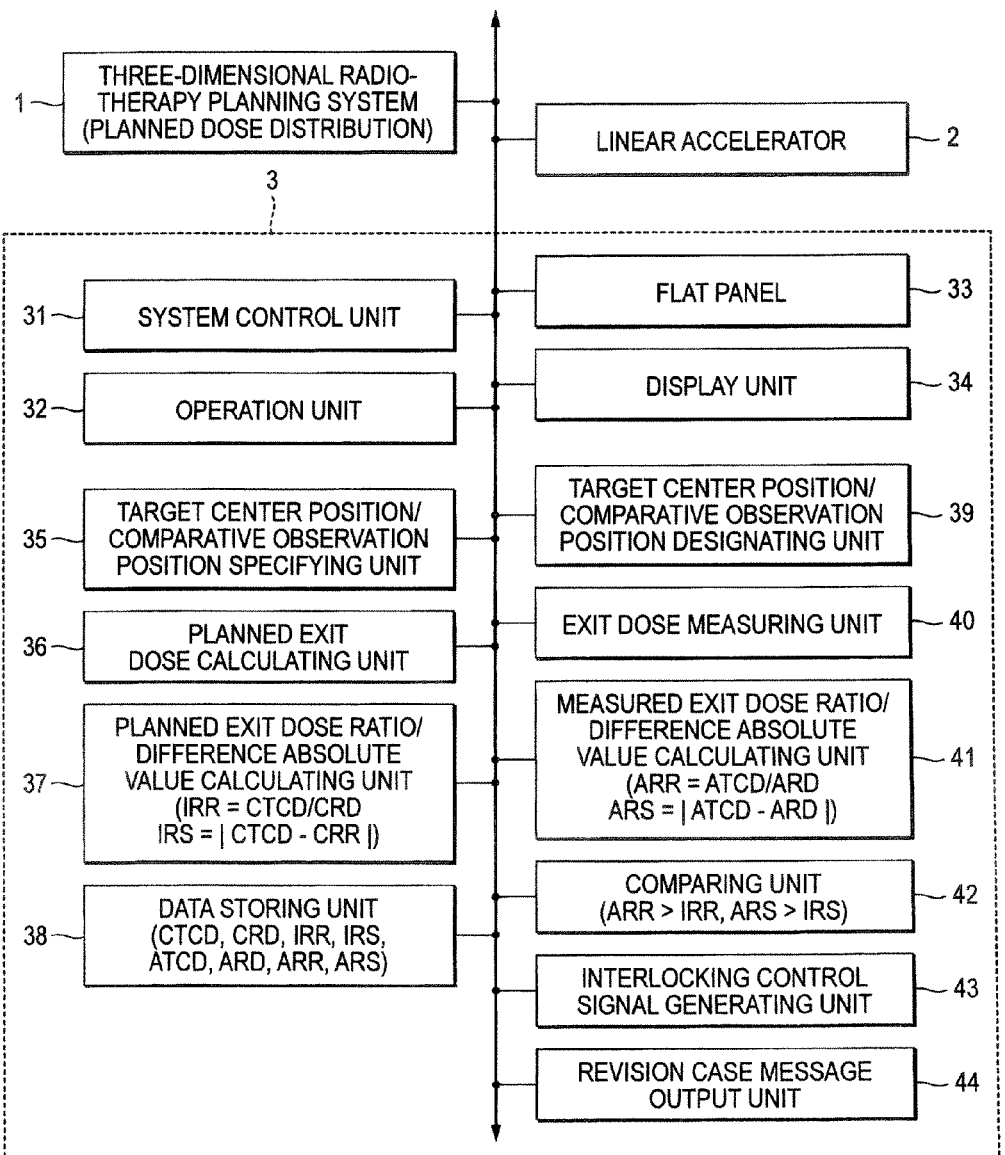
FIG. 1 is a diagram showing a structure of a radiotherapy monitoring apparatus according to an embodiment of the invention.
Figure 2:
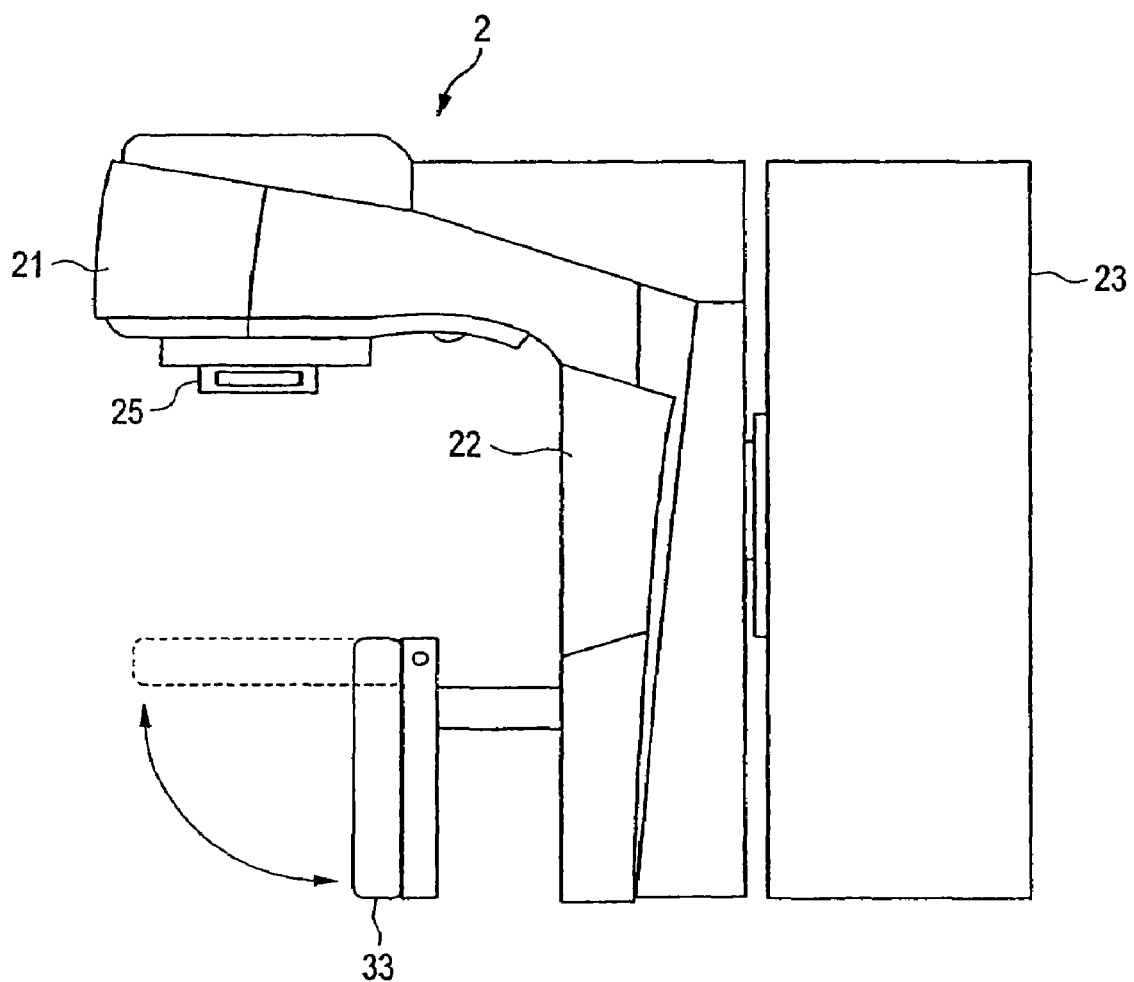
FIG. 2 is a diagram showing a linear accelerator and a flat panel detector in FIG. 1.

A radiotherapy monitoring apparatus according to an embodiment of the invention will be hereinafter explained. A radiotherapy monitoring apparatus 3 is shown in FIG. 1 together with a three-dimensional radiotherapy planning system 1 and a linear accelerator (a radiotherapy apparatus) 2. The radiotherapy monitoring apparatus 3 constitutes a radiotherapy system together with the three-dimensional radiotherapy planning system 1 and the linear accelerator 2. The three-dimensional radiotherapy planning system 1 has a function for calculating an exposure dose distribution on the basis of a scheduled treatment plan and placing the exposure dose distribution over a two-dimensional or three-dimensional image generated in a diagnostic image generating apparatus such as an X-ray computerized tomographic apparatus. As illustrated in FIG. 2, the linear accelerator 2 has a head 21 for irradiating radiations in which an electron gun, an accelerating tube, and the like are housed. A collimator 25 for forming an irradiation field is attached to the head 21. The head 21 is supported by a floor stand 23 via a rotation arm 22 of a substantially L shape.

Figure 3:
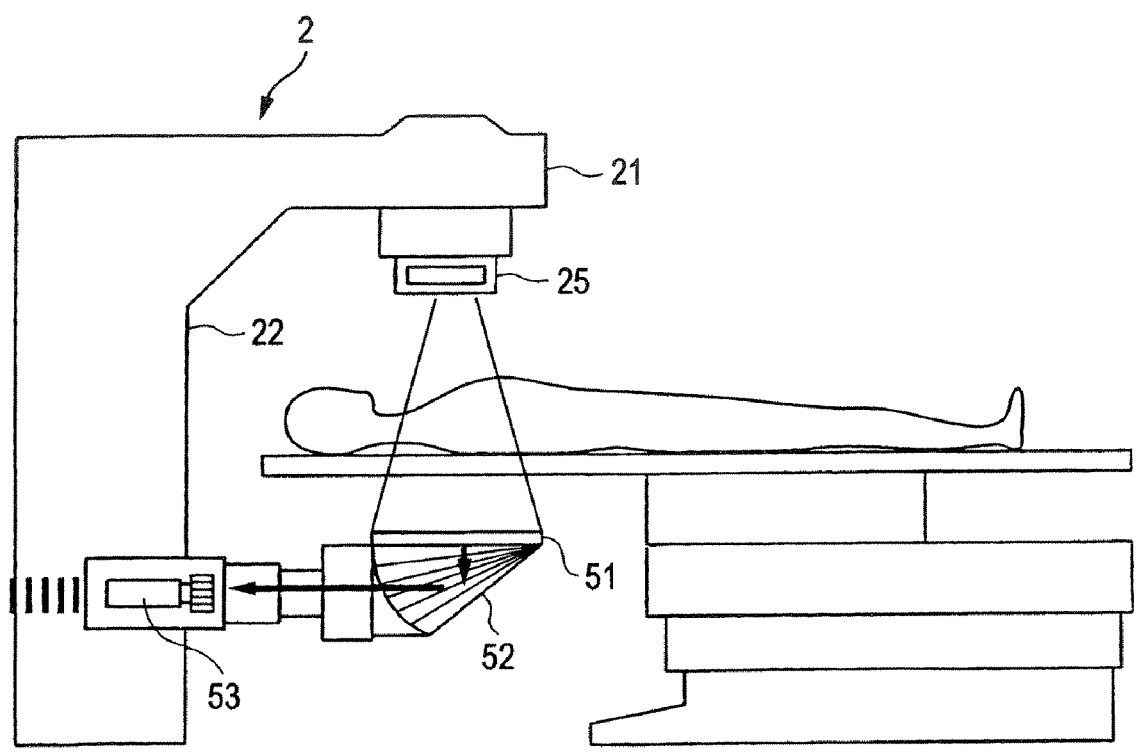
FIG. 3 is a diagram showing a CCD camera system in which the flat panel detector in FIG. 2 can be replaced.

A flat panel detector 33 is attached to the rotation arm 22 to be opposed to the head 21. The flat panel detector 33 has plural detection elements arrayed in a two-dimensional shape that directly convert radiations transmitted through a patient into electric signals (electric charges). An exposure dose distribution can be measured by the detection elements. The flat panel detector 33 may be fixed in a position opposed to the head 21 or may be provided to freely close and open as shown in FIG. 2. As shown in FIG. 3, the flat panel detector 33 can be replaced with a combination of a fluorescent screen 51, an optical system 52, and a CCD camera 53. However, the flat panel detector 33 is superior in terms of spatial resolution, sensitivity, uniformity, distortion, linearity of signal intensity with respect to incident radiation intensity, and the like.

The radiotherapy monitoring apparatus 3 is connected to the three-dimensional radiotherapy planning system 1 and the linear accelerator 2. The radiotherapy monitoring apparatus 3 is provided in order to monitor a treatment state, or instantaneously monitor, during a treatment period, whether an exposure dose has exceeded a planned dose and a durable dose in an irradiation region. Actually, the exposure dose is estimated from a measurable exit dose (a transmitted radiation dose). In that case, the exit dose fluctuates because of labile factors such as deviation of a position of a patient due to body movement with respect to the a radiation irradiation field. In order to allow the fluctuation as much as possible and improve monitoring accuracy, in this embodiment, an exit dose in the irradiation center is standardized by an exit dose in a comparative position set in a dangerous region or the like planned to be irradiated in a low exposure dose in which an influence of exposure should typically be avoided as much as possible. The standardized index is compared with a reference value determined in advance to monitor a treatment state. It is possible to realize further qualitative improvement of treatment by determining the reference value from a dose distribution according to a treatment plan. Moreover, it is possible to substantially directly use a detection value of the flat panel detector 33 for treatment monitoring processing by monitoring a treatment state using an exit dose rather than an exposure dose and an absorbed dose. Consequently, instantaneousness of the treatment monitoring is improved.

The radiotherapy monitoring apparatus 3 has, with a system control unit 31 as a center, an operation unit 32 such as a keyboard or a mouse, the flat panel detector 33, and a display unit 34.

The radiotherapy monitoring apparatus 3 has, as units for determining a reference value for judgment of suitability of a treatment state, a target center position/comparative observation position specifying unit 35, a planned exit dose calculating unit 36, and a planned exit dose ratio/difference absolute value calculating unit 37. The target center position/comparative observation position specifying unit 35 specifies, on the basis of an exposure dose distribution planned by the three-dimensional radiotherapy planning system 1, a target center position and a comparative observation position serving as positions for calculating a reference value. The planned exit dose calculating unit 36 calculates, on the basis of the exposure dose distribution from the three-dimensional radiotherapy planning system 1, a planned exit dose in the target center position (CTCD) specified by the target center position/comparative observation position specifying unit 35 and a planned exit dose in the comparative observation position (CRD). The planned exit dose ratio/difference absolute value calculating unit 37 calculates a ratio of the planned exit doses in the target center position and the comparative observation position (IRR=CTCD/CRD) and an absolute value of a difference between the exit doses (IRS=|CTCD−CRD|).

The ratio of the planned exit doses in the two places (IRR) and the absolute value of the difference between the planned exit doses (IRS) are referred to as reference relative values. During a treatment monitoring period, measured absolute values are compared with the reference relative values. According to the comparison, it is possible to judge whether a radiotherapy operation during a radiotherapy period is progressing as planned. The measured relative values include a ratio of exit doses (ARR) and an absolute value of a difference between the exit doses (ARS) calculated from measured exit doses.

Data of the ratio of the planned exit doses (IRR) and data of the absolute value of the difference (IRS) set as reference values are associated with treatment identification codes and stored in a data storing unit 38 together with data of the planned exit doses (CTCD and CRD).

Moreover, the radiotherapy monitoring apparatus 3 has, as a monitoring unit during the radiotherapy period, a target center position/comparative observation position designating unit 39, an exit dose measuring unit 40, a measured exit dose ratio/difference absolute value calculating unit 41, a comparing unit 42, an interlocking signal control signal generating unit 43, and a revision case message output unit 44. The monitoring unit judges whether a radiotherapy operation is normally progressing in accordance with a plan by measuring exit doses in positions substantially identical with the target center position and the comparative observation position anatomically (for convenience of explanation, hereinafter referred to as target center position and comparative observation position), calculating a ratio of exit doses (ARR) and an absolute value of a difference between exit doses (RS) from the measured values, and comparing the ratio of exit doses and the absolute value of difference between exit doses with the reference values.

In the radiotherapy, the positions substantially identical with the target center position and the comparative observation position, which are specified by the target center position/comparative observation position specifying unit 35 at the time of treatment planning, anatomically are typically designated manually via the operation unit 32. Information on the positions is inputted via the target center position/comparative observation position designating unit 39. The exit dose measuring unit 40 measures, on the basis of data representing exit dose distributions repeatedly outputted from the flat panel detector 33 at a predetermined period, exit doses (ATCD and ARD) in the target enter position and the comparative observation position designated during the radiotherapy period and repeats the measurement. The measured exit dose ratio/difference absolute value calculating unit 41 calculates a ratio of the exit dose in the target center position measured (ATCD) and the exit dose in the comparative observation position measured (ARD) (ARR=ATCD/ARD) and an absolute value of a difference between the exit doses (ARS=|ATCD−ARD|). Data of the ratio of the planned exit doses (ARR) and data of the absolute value of the difference (ARS) set as the measured values are associated with treatment identification codes and time codes representing elapsed times from start of treatment and stored in the data storing unit 38 together with data of the exit doses measured (ATCD and ARD). The comparing unit 42 compares the ratio of the exit doses in the target center position and the comparative observation position measured (ARR) with the ratio of the planned exit doses (IRR) set as the reference value and compares the absolute value of the difference between the exit doses in the target center position and the comparative observation position measured (ARS) with the absolute value of the difference (IRS) set as the reference value.

When the ratio of the measured exit doses (ARR) is inconsistent with the ratio of the planned exit doses (IRR), it is likely that the radiotherapy operation is not normally progressing as planned. In particular, when the ratio of the measured exits doses (ARR) exceeds the ratio of the planned exit doses (IRR), it is judged that an abnormal state in which the radiotherapy operation is not normally progressing because of positional deviation of the patient, fluctuation in an emission dose, or the like occurs at relatively high probability. The increase in the ratio of the measured exit doses (ARR) means that a situation in which an exit dose increases on an axis passing the target center position compared with the comparative observation position occurs or a situation in which an exit dose decreases on an axis passing the relative observation position (typically set in a dangerous region where it is desired to hold down exposure) compared with the target center position occurs.

When the absolute value of the difference between the measured exit doses (ARS) is inconsistent with the absolute value of the difference between the planned exit doses (IRS), it is likely that the radiotherapy operation is not normally progressing. In particular, when the absolute value of the difference between the measured exit doses (ARS) exceeds the absolute value of the difference between the planned exit doses (IRS), it is judged that an abnormal situation occurs at high probability. The increase in the absolute value of the difference between the measured exit doses (ARS) means that an exit dose excessively fluctuates with respect to a planned exit dose on at least one of an axis passing the comparative observation position and an axis passing the target center position.

When at least one of a judgment result in which the ratio of the measured doses (ARR) exceeds the ratio of the planned exit doses (IRR) and a judgment result in which the absolute value of the difference between the measured exit doses (ARS) exceeds the absolute value of the difference between the planned exit doses (IRS) occurs, the interlocking control signal generating unit 43 generates an interlocking control signal for stopping irradiation of radiations on the patient. The linear accelerator 2 stops the generation of radiations with the reception of the interlocking control signal as an opportunity.

When at least one of a judgment result in which the ratio of the measured doses (ARR) exceeds the ratio of the planned exit doses (IRR) and a judgment result in which the absolute value of the difference between the measured exit doses (ARS) exceeds the absolute value of the difference between the planned exit doses (IRS) occurs, the revision case message output unit 44 urgently stops the treatment and generates a control signal for displaying a message for urging an operator to reexamine the treatment on the display unit 34.

Figure 4:
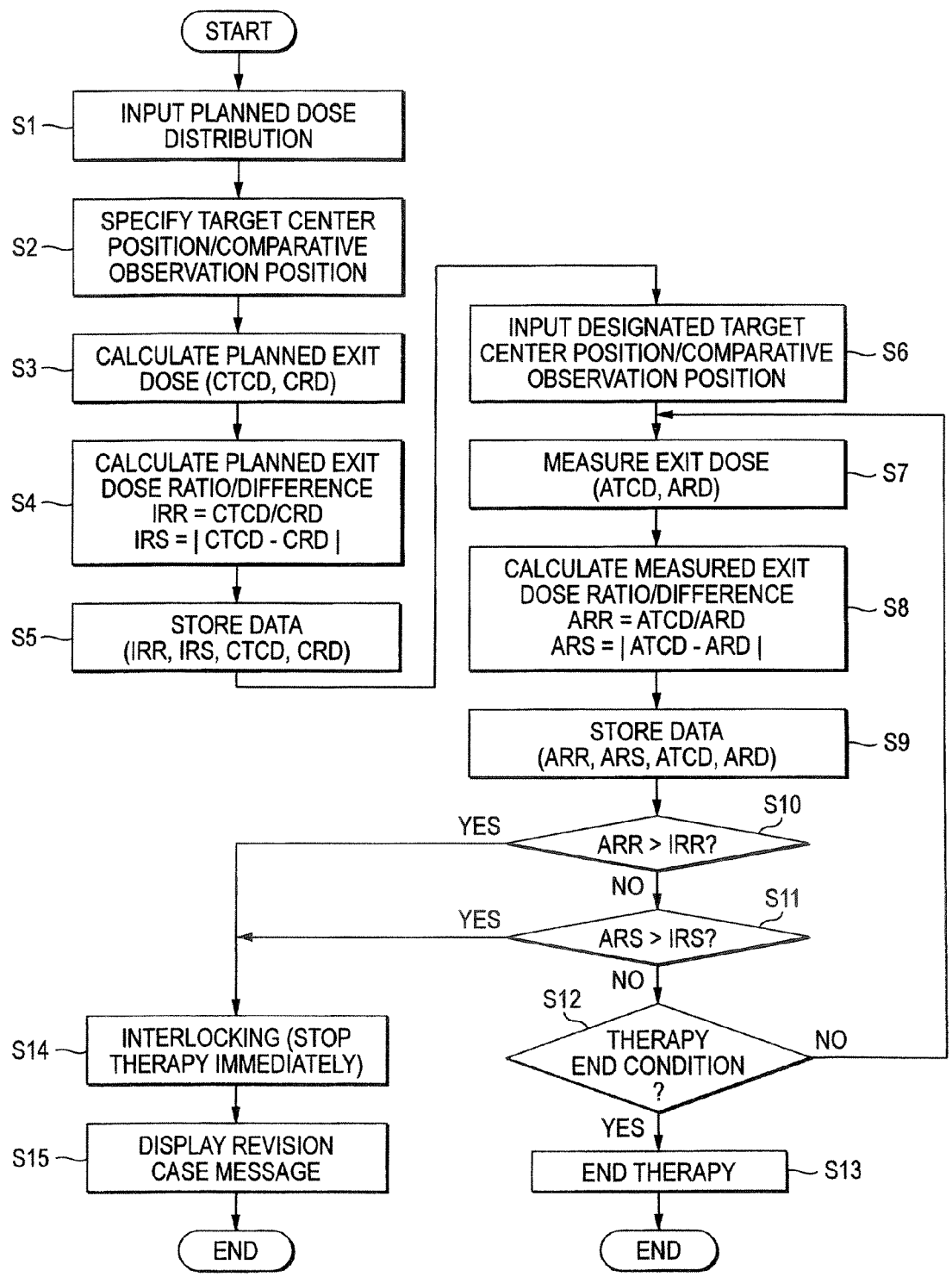
FIG. 4 is a flowchart showing a monitoring operation procedure of radiotherapy in the embodiment.
Figure 5:
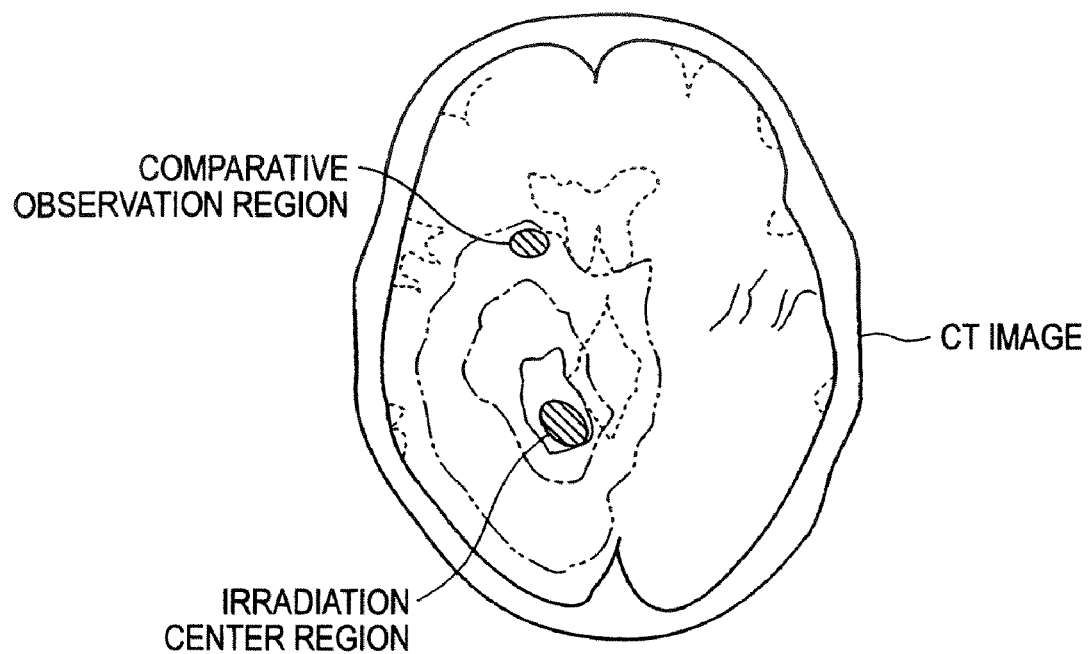
FIG. 5 is a supplementary diagram for S2 and S6 in FIG. 4.

A procedure of a monitoring operation according to this embodiment is shown in FIG. 4. The radiotherapy monitoring apparatus 3 inputs data of a planned exposure dose distribution (dose distribution) from the three-dimensional radiotherapy planning system 1 (S1). In the dose distribution, a spatial distribution of doses is represented by a contour line as illustrated in FIG. 5. The target center position/comparative observation position specifying unit 35 specifies a target center position and a relative observation position (S2). First, in a treatment plan, it is planned to irradiate radiations from a large number of suitable directions with a treatment object region as the center. A converging point of a center axis of the radiations is the target center position. The planned exit dose calculating unit 36 calculates an exit dose in the target center position (CTCD) by subtracting a sum of absorbed doses on an axis passing the target center position from an exposure dose to the position obtained from the dose distribution (S3). It may be advantageous for improvement of monitoring accuracy to calculate the exit dose (CTCD) for a position different from the target center position. For example, the exit dose (CTCD) may be calculated in a position designated by the operator via the operation unit 32. It is also possible that a local region of a predetermined radius is defined with the target center position as the center, a position indicating a minimum dose in the local region is specified, and the exit dose (CTCD) is calculated in the position. Similarly, the comparative observation position preferably set in a region highly likely to be exposed. For example, the operator may designate the comparative observation position as a point via the operation unit 32. It is also possible that a position indicating a maximum dose in the comparative observation area corresponding to the dangerous region designated by the operator via the operation unit 32 is searched for and the position is specified as the comparative observation position. The planned exit dose calculating unit 36 calculates the exit dose (CRD) in the comparative observation position specified (S3).

The planned exit dose ratio/difference absolute value calculating unit 37 calculates, from the exit dose in the target center position (CTCD) and the exit dose in the comparative observation position (CRD) calculated in the planned exit dose calculating unit 36, a ratio of the exit doses (IRR=CTCD/CRD) and an absolute value of a difference between the exit doses (IRS=|CTCD−CRD|) as reference values, respectively (S4). Data of a ratio of exit doses between two points (IRR) and data of an absolute value of a difference between two points in a treatment plan are associated with treatment identification code and stored in the data storing unit 38 together with data of the exit dose in the target center position (CTCD) and data of the exit dose in the comparative observation position (CRD) in the data storing unit 38 (S5).

After the completion of the preparation, at appropriate time when a treatment start trigger is pressed, radiotherapy is started according to the treatment plan. During a period of the radiotherapy, on the basis of an output of the flat panel detector 33, the radiotherapy monitoring apparatus 3 repeatedly calculates measured exit doses (ATCD and ARD) instantaneously in two places substantially identical with the target center position and the comparative observation poison, which are used for the reference value calculation, anatomically. The radiotherapy monitoring apparatus 3 calculates a ratio of the exit doses (ARR) and an absolute value of a difference between the exit doses (ARS) from the exit doses. The radiotherapy monitoring apparatus 3 compares the ratio of the exit doses (ARR) and the absolute value of the difference between the exit doses (ARS) with the ratio of exit doses (IRR) and the absolute value of the difference between the exit doses (IRS) set as the reference values to monitor a treatment state. Details of the monitoring operation will be hereinafter explained in detail.

In treatment, positions corresponding to the target center position and the comparative observation position specified in the S2, respectively, are designated via the operation unit 32 on, for example, an image formed according to an output of the flat panel detector 33 (S6). The exit dose measuring unit 40 measures, on the basis of the output of the flat panel detector 33, exit doses (ATCD and ARD) in the target center position and the comparative observation position designated in S6 (S7). The measured exit dose ratio/difference calculating unit 41 calculates, from the exit does in the target center position (ATCD) and the exit dose in the comparative observation position (ARD) measured, a ratio of the measured exit doses (ARR=ATCD/ARD) and an absolute value of a difference between the measured exit doses (ARS=|ATCD−ARD|) (S8). Data of the ratio of the measured exit doses (ARR) and data of the absolute value of the difference between the measured exit doses (ARS) are associated with treatment identification codes and time codes representing elapsed times from start of treatment and stored in the data storing unit 38 together with data of the measured exit doses (ATCD and ARD) (S9).

The comparing unit 42 compares the ratio of the exit doses (ARR) in the target center position and the comparative observation position measured with the ratio of the planned exit doses (IRR) set as the reference value (S10). Similarly, the comparing unit 42 compares the absolute value of the difference between the exit doses (ARS) in the target center position and the comparative observation position measured with the absolute value of the difference between the planned exit doses (IRS) set as the reference value (S11).

When at least one of a judgment result in which the ratio of the measured doses (ARR) exceeds the ratio of the planned exit doses (IRR) and a judgment result in which the absolute value of the difference between the measured exit doses (ARS) exceeds the absolute value of the difference between the planned exit doses (IRS) occurs, judging that it is highly likely that abnormality occurs in the treatment, the interlocking control signal generating unit 43 generates an interlocking control signal for stopping irradiation of radiations on the patient (S14). The revision case message output unit 44 generates a control signal for indicating that the treatment is urgently stopped and displaying a message for urging the operator to reexamine the treatment on the display unit 34 (S15). Consequently, the irradiation of radiations on the patient is stopped and the operator can recognize that the treatment is urgently stopped and it is necessary to reexamine the treatment.

When the ratio of the measured doses (ARR) does not exceed the ratio of the planned exit doses (IRR) and the absolute value of the difference between the measured exit doses (ARS) does not exceed the absolute value of the difference between the planned exit doses (IRS), it is judged that the treatment is normally progressing as planned and the processing from S7 to S11 is repeated until a planned treatment end condition is satisfied (S12 and S13).

As described above, according to this embodiment, it is possible to monitor a treatment state highly accurately and instantaneously. With a ratio of an exit dose in an irradiation center and an exit dose in a comparative position and an absolute value of a difference between the exit doses set as indexes, a treatment state is monitored by comparing the indexes with reference values. The reference values are determined from a dose distribution according to a treatment plan. Consequently, it is possible to realize the effects and, therefore, it is possible to realize qualitative improvement of the treatment. Moreover, since the treatment state is monitored using an exit dose rather than an exposure dose and an absorbed dose, it is possible to substantially directly use a detected value of the flat panel detector 33 and improve instantaneousness of the treatment monitoring.

Figure 6A:
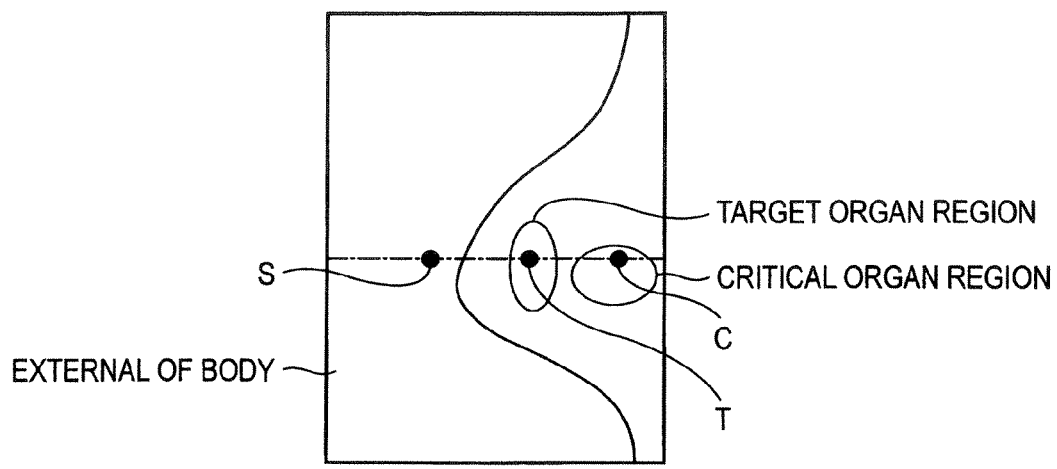
FIG. 6A is a diagram showing three points of a target organ region, a critical organ region, and an external of body as a modification of S2 and S6 in FIG. 4.

In the above description, relative values between the two points, that is, the target center position and the comparative observation position, and a treatment state is monitored according to the relative values. However, a relative ratio among three points may be calculated to monitor a treatment state according to the relative ratio. For example, as illustrated in FIG. 6A, a position T in a target organ region, a position C outside the target organ region and in a critical organ region having relatively high sensitivity to radiations, and a position in an external of body (a reference position) S are set. Typically, the positions T, C, and S are linearly arranged. When it is assumed that a dose in the target position T, a dose in the critical position C, and a dose in the external position S measured by the flat panel detector 33 are DT, DC, and DS, respectively, a ratio of the measured doses ARR is typically calculated as follows.

$$ARR = |DT/DS - DC/DS|$$

The ratio of the measured doses ARR is calculated as an absolute value of a difference between a ratio of the dose DT in the target position T with respect to the dose DS in the external position S and a ratio of the dose DC in the critical position C with respect to the dose DS in the external position S. It is possible to perform the monitoring highly accurately by comparing the ratio of the measured doses ARR with respect to the three points with a planned ratio of doses IRR concerning the same three points.

Figure 6B:
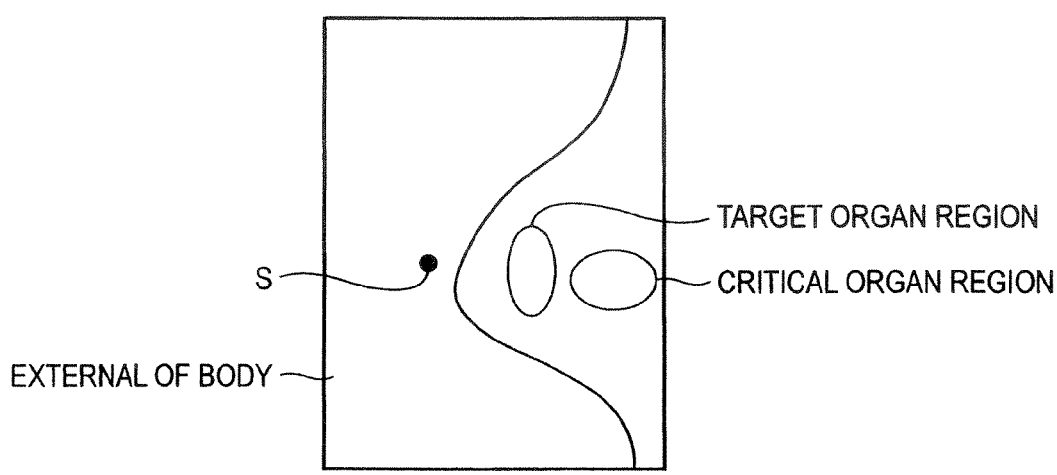
FIG. 6B is a diagram showing a target organ region, a critical organ region, and an external of body as a modification of S2 and S6 in FIG. 4.

As shown in FIG. 6B, it is also possible that an average of doses in a target organ region is calculated as $D_T$, an average of doses in a critical organ region is calculated as $D_C$, and IRR and ARR are calculated according to the above equation.

This embodiment is a real time dose monitoring device that prevents a setup error in a breast cancer patient using the flat panel detector 33. It is possible to improve daily patient setup accuracy and prevent irregular irradiation. As a characteristic of this embodiment, a ratio among the respective point is used instead of an absolute dose.

The invention is not limited to the embodiment itself. The elements of the invention may be modified and embodied without departing from the spirit of the invention in an implementation stage. Various inventions can be formed according to appropriate combinations of the plural elements disclosed in the embodiment. For example, some elements may be deleted from all the elements described in the embodiment. Elements described in different embodiments may be appropriately combined.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A radiotherapy monitoring apparatus for monitoring a treatment state by irradiation of radiations on a treatment region, comprising:
   a detecting unit configured to detect the radiations transmitted through the treatment region at least in two places;
   a comparing unit configured to compare a relative value of the transmitted radiations in the two places with a reference relative value; and
   a control signal generating unit configured to generate, when the relative value exceeds the reference relative value, a control signal for stopping the irradiation of the radiations, the relative value being at least one of a ratio of transmitted doses in the at least two places and an absolute value of a difference between the transmitted doses.

2. A radiotherapy monitoring apparatus according to claim 1, wherein the detecting unit is a flat panel detector.

3. A radiotherapy monitoring apparatus according to claim 1, wherein the detecting unit directly converts the radiations into electric signals.

4. A radiotherapy monitoring apparatus according to claim 1, wherein a position in the treatment region is included in the two places.

5. A radiotherapy monitoring apparatus according to claim 1, wherein a position in the treatment region and a position outside the treatment region are included in the two places.

6. A radiotherapy monitoring apparatus according to claim 1, wherein the control signal generating unit generates the control signal when at least one of the ratio of the transmitted doses and the absolute value of the difference exceeds the reference relative value.

7. A radiotherapy monitoring apparatus according to claim 1, wherein, when it is assumed that a dose in a position in the treatment region is DT, a dose in a position outside the treatment region and in a critical organ region having relatively high sensitivity to radiations is DC, and a dose in an external position of a patient is DS, the relative value is calculated by |DT/DS−DC/DS|.

8. A radiotherapy monitoring apparatus according to claim 1, wherein the control signal corresponds to display of a message for urging an operator to reexamine a treatment plan.

9. A radiotherapy monitoring apparatus for monitoring a treatment state by irradiation of radiations on a treatment region, comprising:
- a reference value calculating unit configured to calculate at least one of a ratio of exit doses in at least two places in an irradiation range of the radiations and an absolute value of a difference between the exit doses as a reference value on the basis of a planned dose distribution;
- a detecting unit configured to detect the radiations transmitted through the treatment region;
- a measured value calculating unit configured to calculate at least one of the ratio of the exit doses in the two places and the absolute value of the difference between the exit doses as a measured value on the basis of an output of the detecting unit;
- a comparing unit configured to compare the measured value with the reference value; and
- a control signal output unit configured to output a control signal corresponding to a result obtained by comparing the measured value with the reference value.

10. A radiotherapy monitoring apparatus according to claim 9, wherein the control signal corresponds to urgent stop of the irradiation of the radiations.

11. A radiotherapy monitoring apparatus according to claim 9, wherein the control signal corresponds to display of a message for urging an operator to reexamine a treatment plan.

12. A radiotherapy monitoring apparatus according to claim 9, wherein one of the two places is set in a target center position region and the other of the two places is set in a comparative observation position region.

13. A radiotherapy monitoring apparatus according to claim 9, wherein one of the two places is a place where an exposure dose indicates a minimum in a target center position region and the other of the two places is a place where an exposure dose indicates a maximum in a comparative observation position region.

14. A radiotherapy monitoring apparatus according to claim 9, further comprising an operation unit with which an operator performs operation for designating the two places.

15. A radiotherapy monitoring apparatus according to claim 9, wherein the control signal output unit generates the control signal when the ratio of the exit doses calculated by the measured value calculating unit exceeds the ratio of the exit doses calculated by the reference value calculating unit.

16. A radiotherapy monitoring apparatus according to claim 9, wherein the control signal output unit generates the control signal when the absolute value of the difference between the exit doses calculated by the measured value calculating unit exceeds the absolute value of the difference between the exit doses calculated by the reference value calculating unit.

17. A radiotherapy monitoring apparatus according to claim 9, wherein the control signal output unit generates the control signal when at least one of a state in which the ratio of the exit doses calculated by the measured value calculating unit exceeds the ratio of the exit doses calculated by the reference value calculating unit and a state in which the absolute value of the difference between the exit doses calculated by the measured value calculating unit exceeds the absolute value of the difference between the exit doses calculated by the reference value calculating unit occurs.

18. A radiotherapy monitoring apparatus according to claim 9, wherein the detecting unit has plural detecting elements arrayed in a two-dimensional shape for directly converting the radiations into electric signals.

19. A radiotherapy monitoring apparatus according to claim 9, further comprising a data storing unit that stores data of the measured value together with a measurement date and time.

20. A radiotherapy monitoring apparatus for monitoring a treatment state by irradiation of radiations on a treatment region, comprising:
- a detecting unit configured to detect the radiations transmitted through the treatment region;
- a calculating unit configured to calculate at least one of a ratio of exit doses in at least two places in an irradiation range of the radiations and an absolute value of a difference between the exit doses as a measured value on the basis of an output of the detecting unit;
- a comparing unit configured to compare the measured value with a predetermined value; and
- a signal output unit configured to output a control signal corresponding to a result of the comparison of the measured value with the predetermined value.

* * * * *